(12) United States Patent
Kaushik et al.

(10) Patent No.: US 6,781,003 B1
(45) Date of Patent: Aug. 24, 2004

(54) PREPARATION OF PURE CITALOPRAM

(75) Inventors: Vipin Kumar Kaushik, Hyderabad (IN); Divvela Venkata Naga Srinivasa Rao, Hyderabad (IN); Vijay Kumar Handa, Hyderabad (IN); Meenakshisunderam Sivakumaran, Hyderabad (IN)

(73) Assignee: Aurobindo Pharma Ltd., Hyderabad (IN)

( * ) Notice: Subject to any disclaimer, the term of this patent is extended or adjusted under 35 U.S.C. 154(b) by 0 days.

(21) Appl. No.: 10/456,135

(22) Filed: Jun. 9, 2003

(51) Int. Cl.[7] .............................................. C07D 307/78

(52) U.S. Cl. ....................................... 549/467; 549/469

(58) Field of Search ................................. 549/467, 469

(56) References Cited

U.S. PATENT DOCUMENTS 6,258,842 B1 * 7/2001 Petersen et al. ............ 514/469
6,291,689 B1 * 9/2001 Petersen et al. ............ 549/467

* cited by examiner

*Primary Examiner*—Amelia A. Owens
(74) *Attorney, Agent, or Firm*—Jay R Akhave

(57) ABSTRACT

The present invention relates to an industrially advantageous method for the purification of Citalopram (Formula I) wherein desmethyl citalopram (Formula II), present in crude Citalopram as an impurity, is methylated to produce pure Citalopram. The resulting Citalopram product is isolated as the base or a pharmaceutically acceptable salt thereof

FORMULA I

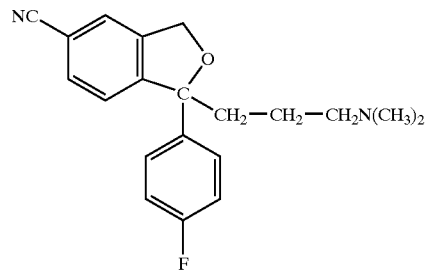

FORMULA II

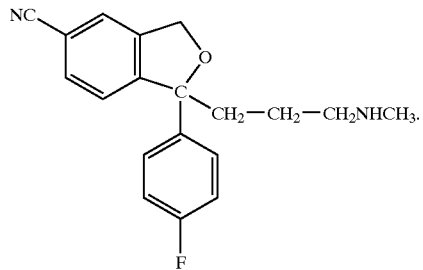

4 Claims, No Drawings

PREPARATION OF PURE CITALOPRAM

CROSS REFERENCE TO RELATED APPLICATIONS

Indian Patent Application
Filing Date Mar. 19, 2003
Application No. 225/MAS/2003
Status Not issued

STATEMENTS REGARDING FEDERALLY SPONSORED RESEARCH AND DEVELOPMENT

Not Applicable

BACKGROUND OF THE INVENTION

Citalopram of Formula I is a well known antidepressant drug that has now been on the market for several years and is chemically known as 1-[3-(dimethylamino)propyl]-1-(4-fluorophenyl)-1,3-dihydroisobenzofuran-5-carbonitrile.

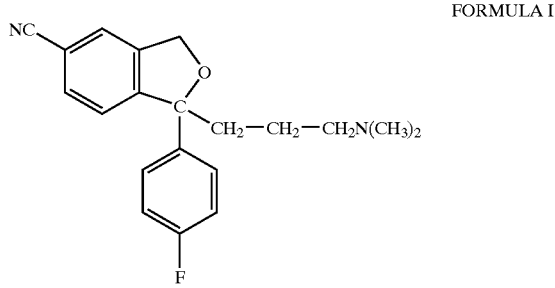

FORMULA I

Citalopram is a selective centrally acting serotonin reuptake inhibitor and it has further been shown to be effective in the treatment of dementia and cerebrovascular disorder as described in European Patent 0 474 580.

Citalopram was first disclosed in U.S. Pat. No. 4,136,193. This patent publication outlines a process for preparation of Citalopram from corresponding 5-bromo derivative by reaction with cuprous cyanide. Further, variants of this method are disclosed in PCT Applications, WO 00/13648 and WO 00/11926 wherein the exchange of 5-nalogen or 5-$CF_3$—$(CF_2)_n$—$SO_2$—O—with cyano is achieved with cyanide source in the presence of palladium or nickel catalyst.

The processes comprising exchange of 5halogen with cyano as described above have been found to give high molecular weight impurities and desmethyl citalopram in unacceptable quantities. PCT Application WO 01/47877 describes a process of film distillation to remove high molecular weight impurities formed during cyanide exchange reaction, however, desmethyl citalopram distils along with Citalopram. Removal of desmethyl impurity by usual purification procedures, such as recrystallization, distillation, reprecipitation, washing, salt formation or the like, is difficult and requires extensive and expensive purification processes.

PCT Application WO 01/45483 teaches an acylation method that effectively removes desmethyl citalopram. This comprises treating the crude product with an acylating agent such as an acid anhydride or an acid halide wherein desmethyl citalopram forms an amide derivative and is removed by acid/base wash followed by crystallization to obtain pure Citalopram. While desmethyl citalopram gets removed in this process as an amide derivative, yield loss coupled with purification involving a chemical step makes this process untenable to operate on industrial scale.

It is an object of the present invention to devise a simple and commercially attractive process for removing desmethyl impurity. It has been found that crude Citalopram containing desmethyl impurity can be methylated to produce highly pure Citalopram in high yield.

DETAILED DESCRIPTION OF THE INVENTION

The instant invention relates to a novel process whereby the desmethyl citalopram impurity (Formula II), present in crude Citalopram, is transformed to Citalopram by methylation to produce pure Citalopram (Formula I).

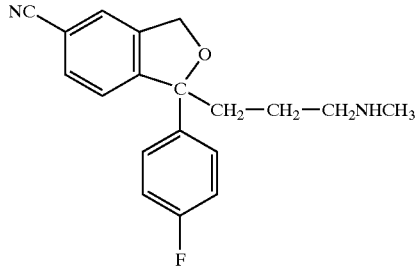

FORMULA II

Specifically, the present invention involves reacting crude Citalopram with formaldehyde and formic acid to accomplish the methylation of desmethyl impurity to obtain pure Citalopram. This purification method of Citalopram is simple and efficient and provides quantitative conversion of desmethyl citalopram into Citalopram thereby resulting in increased Citalopram yield.

The crude Citalopram of Formula I may be prepared by the cyanide exchange reaction of corresponding 5-bromo derivative as described in U.S. Pat. No. 4,136,193. The methylation is carried out by treating the crude Citalopram with formaldehyde and formic acid. Formaldehyde employed in the methylation reaction is 35% aqueous solution and is used in an amount up to 3 moles per mole of desmethyl content present in crude Citalopram. Formic acid is used up to 6 moles per mole of desmethyl content The said reaction is conducted in neat without adding any solvent. Typically, the methylation is completed by heating crude Citalopram with formaldehyde and formic acid at a temperature of 85–95° C. for 30 min.

After methylation, the reaction mass as such is diluted with ethanol and oxalic acid is added to isolate Citalopram oxalate which is free from desmethyl impurity. The oxalate salt can further be crystallized from ethanol to consistently attain more than 99.5% purity.

The major advantage realized in the present purification process as compared to prior art of removing desmethyl impurity is the increased process productivity as impurity is converted to the Citalopram. Moreover, no additional chemical/isolation step is needed to remove desmethyl impurity. Also, this procedure demonstrates a greater efficiency than the prior art.

The Citalopram oxalate thus obtained can be converted to pharmaceutically acceptable highly pure Citalopram hydrobromide salt by the conditions well known in the art.

Crude Citalopram can be prepared by known methods. The following procedure was adopted to prepare crude citalopram which was then purified as shown in Example 1 using our inventive technique. Further, details of the present invention are to be found in Examples 1 and 2 without limiting it.

Preparation of Crude Citalopram

Cuprous cyanide (85.4 g, 0.95 mol) was added to 5-bromo-1-(3-dimethylaminopropyl) 1-(4-fluorophenyl)-1, 3-dihydroisobenzofuran (200 g, 0.53 mol) and contents were heated to 140–150° C. After completion of reaction, N,N-dimethylformamide (200 ml) was added and reaction mass was further diluted with toluene (500 ml). The reaction mixture was cooled to 80° C. where aqueous ethylenediamine (50% w/v) was added and layers were separated. The organic layer was washed sequentially with aqueous EDTA (2% w/v) and water (2×200 ml). The organic layer was concentrated under reduced pressure to remove toluene. The residue was distilled in vacuum and crude Citalopram was obtained as oil. Yield: 110 g. The crude product contained 7% of desmethyl citalopram by HPLC.

EXAMPLE 1

Purification of Crude Citalopram

To the crude Citalopram (90 g, 0.28 mol) having desmethyl citalopram (7%, HPLC), formic acid (98%, 2.7 g) was added followed by aqueous formaldehyde (35%, 2.37 g). The reaction mass was heated at 85–95° C. for 30 min. HPLC indicated complete conversion of desmethyl impurity into Citalopram. The reaction mass was cooled to 30° C. and diluted with ethanol (900 ml). Oxalic acid dihydrate (41.94 g, 0.33 mol) was added and mass was heated to reflux. The obtained solution was cooled to 20–25° C. and stirring was continued for 2 hours at 20–25° C. The product thus obtained was filtered and crystallized from ethanol to provide highly pure 92 g of crystalline Citalopram oxalate having HPLC purity 99.7% and desmethyl citalopram impurity: Not Detected.

EXAMPLE 2

Subsequent Preparation of Citalopram Hydrobromide from Purified Citalopram

DM water (880 ml) was added to Citalopram oxalate as obtained above (88 g) followed by addition of toluene (700 ml). The pH of the mixture was adjusted to 9.2–9.6 with aqueous ammonia. The organic layer was separated, washed with DM water and thereafter toluene was removed under reduced pressure. Acetone (620 ml) was added to the residue followed by the addition of 48% aqueous hydrobromic acid solution (25 g). The solvent was distilled out under reduced pressure at 30–55° C. Fresh acetone (240 ml) was added and refluxed for 30 min. The reaction mixture was cooled to 5–10° C. and stirred for 5 hours. The crystalline product thus obtained was filtered, washed sequentially with chilled cyclohexane and acetone and dried to obtain Citalopram hydrobromide (79.2 g) having HPLC purity 99.8%.

We claim:

1. A method for the purification of crude citalopram of formula I comprising the steps of:

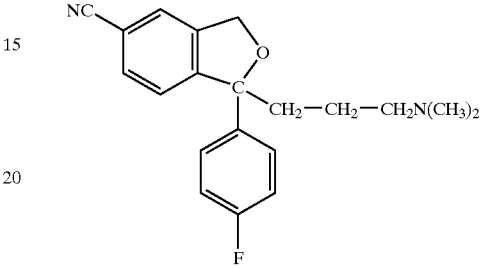

FORMULA I starting with crude Citalopram of Formula I having desmethyl citalopram impurity of Formula II in it,

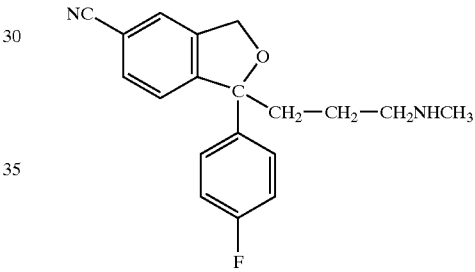

FORMULA II methylating the said impurity to produce pure Citalopram.

2. The process according to claim 1 wherein the said methylation step is carried out with aqueous formaldehyde and formic acid solution.

3. The process according to claim 1 wherein the said methylation step is completed in 30 minutes.

4. The process according to claim 1 where the said methylation step is conducted at temperatures in the range of 85° C. to 95° C.

* * * * *